United States Patent [19]

Welzel et al.

[11] Patent Number: 4,797,404

[45] Date of Patent: Jan. 10, 1989

[54] PHARMACEUTICAL PREPARATION COMPRISING CO-DERGOCRINE AND A CALCIUM ANTAGONIST

[75] Inventors: Dieter Welzel; Hans Bühlmann, both of Nuremberg, Fed. Rep. of Germany

[73] Assignee: Sandoz Ltd., Basel, Switzerland

[21] Appl. No.: 126,663

[22] Filed: Dec. 1, 1987

Related U.S. Application Data

[63] Continuation of Ser. No. 889,160, Jul. 25, 1986, abandoned, which is a continuation of Ser. No. 775,985, Sep. 13, 1985, Pat. No. 4,617,306, which is a continuation of Ser. No. 723,948, Apr. 16, 1985, abandoned, which is a continuation of Ser. No. 601,496, Apr. 18, 1984, abandoned.

[30] Foreign Application Priority Data

Apr. 22, 1983 [DE]  Fed. Rep. of Germany ....... 3314607

[51] Int. Cl.⁴ .............................................. A61K 31/44
[52] U.S. Cl. ..................................... 514/288; 514/356
[58] Field of Search ................................ 514/288, 356

[56] References Cited

FOREIGN PATENT DOCUMENTS 23355  2/1981  European Pat. Off. .
1228618  4/1971  United Kingdom .

OTHER PUBLICATIONS

Curr. Ther. Res., 34, pp. 1014–1022 (1983).
Am. J. Cardiology, 44, pp. 798–803 (1979).
Anaesthesist, 29, pp. 85–88 (1980).
Internist, 23, pp. 610–615 (1982).
Therapiewoche, 33, pp. 3105–3117 (1980).
Japanese Patent Application 120871/77 published May 4, 1979.

Primary Examiner—Stanley J. Friedman
Attorney, Agent, or Firm—Gerald D. Sharkin; Robert S. Honor; Joseph J. Borovian

[57] ABSTRACT

Pharmaceutical preparations comprising (a) co-dergocrine or a pharmaceutically acceptable acid addition salt thereof and (b) a calcium antagonist or a pharmaceutically acceptable salt thereof, as well as the treatment of hypertension/migraine by co-administration of components (a) and (b), e.g. in the form of a composition as defined.

19 Claims, No Drawings

PHARMACEUTICAL PREPARATION COMPRISING CO-DERGOCRINE AND A CALCIUM ANTAGONIST

This is a continuation of application Ser. No. 889,160, filed July 25, 1986 now abandoned, which in turn is a continuation of application Ser. No. 775,985, filed Sept. 13, 1985, now issued as U.S. Pat. No. 4,617,306, which in turn is a continuation of application Ser. No. 723,948, filed Apr. 16, 1985, which in turn is a continuation of application Ser. No. 601,496, filed Apr. 18, 1984, the latter two now abandoned.

The present invention relates to novel pharmaceutical preparations having improved anti-hypertensive properties and comprising a combination of active ingredients, as well as the use of the active ingredients in combination and in particular the use of said compositions in the treatment of hypertension.

Co-dergocrine, which is also known as dihydroergotoxin, is a known, commercially available, pharmaceutically active substance. Animal studies indicate that co-dergocrine rodifies cerebral neurotransmission, and evidence is available for its having a stimulant effect on dopamine and serotonin receptors and for a blocking effect at α-adrenoreceptor sites. It improves impaired cerebral metabolic function, an effect which is reflected in changes in the electrical activity of the brain, notably in electroencephalogram power spectra.

This beneficial effect on the EEG has been confirmed by experimental studies in man. Co-dergocrine has also been found to shorten cerebral circulation time. In clinic co-dergocrine has been found to be effective in improving many of the symptoms of mental deterioration, especially age related symptoms, e.g. in the areas of self-care, social behaviour, emotional state and mental performance. Co-dergocrine has also been found to possess a stabilising effect on the tone of cranial vessels. Given this pharmacological profile, co-dergocrine has found wide-spread application in the treatment of impaired mental function in particular in the elderly.

Chemically, co-dergocrine is a 1:1:1 mixture by weight of dihydroergocryptin, dihydroergocornin and dihydroergocristin, the dihydroergocryotin component being itself a mixture of the α- and α-isomers in a weight ratio of 2:1 (α:β). Co-dergocrine exists in both free and in acid addition salt form. For pharmaceutical application it is generally employed in pharmaceutically acceptable acid addition salt form, in particular in the form of its methanesulfonate, co-dergocrine methanesulfonate, also known as co-dergocrine mesylate (BAN), dihydroergotoxin methanesulfonate, ergoloid mesylates (USAN) and Hydergin ®.Other pharmaceutically acceptable acid addition salts which may be employed include the ethanesulfonate, fumarate, maleinate, tartrate and hydrochloride.

The calcium antagonists comprise a known class of physiologically active substances characterised by their calcium antagonist or calcium blocking activity. A wide range of such compounds are now known and have found wide therapeutic application, in particular in the treatment of cardio-vascular disturbance or disease, for example i the treatment of coronary insufficiency. disturbance in cerebral circulation, hypertension and in the treatment of other disturbances in peripheral circulation. Typically the calcium antagonists are employed as vasodilators, e.g. in the treatment of hypertension.

In accordance with the present invention it has now been found that pharmaceutical preparations comprising (a) co-dergocrine or a pharmaceutically acceptable acid addition salt thereof and (b) a calcium antagonist or pharmaceutically acceptable acid addition salt thereof, possess surprising and unexpected pharmaceutical properties with an especially favourable or improved pharmacological/therapeutic profile. In particular it has been found that administration of a component (a) and a component (b) as aforesaid in conjunction, results in unexpected enhancement of vaso-dilatory/anti-hypertensive activity as may be shown in animal tests as well as in clinical trials, for example as hereinafter described. Co-administration of components (a) and (b) as aforesaid, e.g. in the form of a pharmaceutical preparation, e.g. as hereinafter particularly described, is accordingly of especial utility, e.g. in the treatment of hypertension.

In accordance with the foregoing the present invention provides a pharmaceutical preparation comprising:
(a) co-dergocrine or a pharmaceutically acceptable acid addition salt thereof; and
(b) a calcium antagonist or pharmaceutically acceptable acid addition salt thereof.

In the preparations of the invention, (a) is preferably a pharmaceutically acceptable acid addition salt of co-dergocrine, e.g. as hereinabove described. Most preferably (a) is co-dergocrine mesylate.

Suitable calcium antagonists for use in the preparations of the invention are those of the formula I

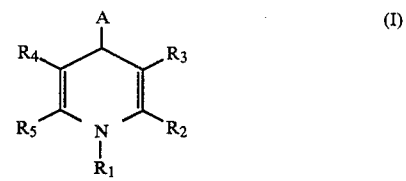

wherein A is a residue of formula (a), (b) or (c)

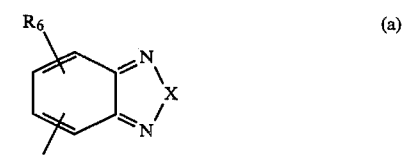

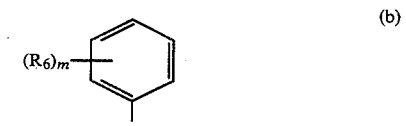

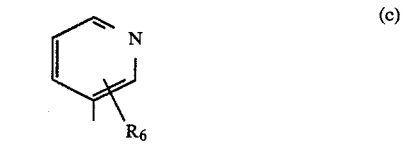

$R_1$ is hydrogen, $(C_{1-6})$alkyl, hydroxy$(C_{2-6})$alkyl, $(C_{3-6})$alkoxyalkyl, $(C_{3-6})$alkenyl, $(C_{3-6})$alkinyl, $(C_{3-7})$cycloalkyl or $(C_{4-8})$cycloalkylalkyl, or $(C_{7-9})$phenylalkyl or $(C_{9-12})$phenylalkenyl, wherein the phenyl ring is unsubstituted or mono-, di- or tri-substituted by halogen, hydroxy, $(C_{1-4})$-alkyl or $(C_{1-4})$alkoxy, $R_2$ and $R_5$ are each independently hydrogen, $(C_{1-6})$alkyl, $(C_{7-10})$phenylalkyl, $(C_{3-7})$cycloalkyl or $(C_{4-8})$cycloalkylalkyl, whereby, when A is a residue b, one of $R_2$ and $R_5$ may also be $(C_{1-4})$hydroxyalkyl or cyano, $R_3$ and $R_4$ are independently —CN, —COOR$_7$, —COR$_8$, —S(O)$_n$R$_9$ or —COO—A—N(R$_{10}$)R$_{11}$, n is 0, 1 or 2, $R_6$ is hydrogen, halogen, $(C_{1-4})$alkyl, $(C_{1-4})$alkoxy, $(C_{1-4})$alkylthio, $(C_{1-4})$alkylsulfonyl, trifluoromethyl, nitro, hydroxy, azido, amino, $(C_{1-4})$alkylamino, di[$C_{1-4}$alkyl]amino, $(C_{1-5})$alkanoylamino, $(C_{2-5})$carbalkoxy, aminocarbonyl, trifluoromethoxy, cyano, sulfamoyl, $(C_{1-4})$alkylsulfamoyl or di[$(C_{1-4})$alkyl]sulfamoyl, X is oxygen or sulphur, m is 0, 1 or 2, $R_7$, and $R_9$ are each independently $(C_{1-6})$alkyl, $(C_{3-6})$alkenyl, $(C_{3-6})$alkinyl, $(C_{3-7})$cycloalkyl, $(C_{4-8})$cycloalkylalkyl, hydroxy-$(C_{2-6})$alkyl, $(C_{3-6})$alkoxyalkyl, hydroxy$(4-8)$alkoxyalkyl, amino-$(C_{2-6})$alkyl, $(C_{1-4})$alkylamino$(C_{2-6})$alkyl, di[$(C_{1-4})$alkyl]aminoalkyl, phenyl, $(C_{7-10})$phenylalkyl, a 5- or 6-membered heterocyclic ring, containing a nitrogen or oxygen or sulphur atom and which may also contain 1, 2 or 3 additional ring nitrogen atoms, or $(C_{1-4})$alkyl optionally substituted by a 5- or 6-membered heterocyclic ring containing a nitrogen or oxygen or sulphur atom as heteroatom and which may additionally contain 1, 2 or 3 further ring nitrogen atoms, whereby, when A is a residue b, $R_7$ may also be trifluoroethyl, A is $(C_{1-6})$alkylene, $R_{10}$ and $R_{11}$ are each independently $(C_{1-6})$alkyl, $(C_{3-6})$alkenyl, $(C_{3-6})$alkinyl, $(C_{3-7})$cycloalkyl, $(C_{4-8})$cycloalkylalkyl, hydroxy$(C_{2-6})$alkyl, $(C_{3-6})$alkoxyalkyl, hydroxy$(C_{4-8})$alkoxyalkyl, amino$(C_{2-6})$alkyl, $(C_{1-4})$alkylamino$(C_{2-6})$alkyl, di[$(C_{1-4})$alkyl]amino-$(C_{1-4})$alkyl, phenyl, or $(C_{7-10})$phenylalkyl, or $R_{10}$ and $R_{11}$ are together with the nitrogen atom to which they are attached comprise a 5-, 6- or 7-membered heterocyclic ring optionally containing a further heteroatom selected from oxygen or sulphur or a group =N—R$_{12}$, wherein R$_{12}$ is $(C_{1-4})$alkyl.

The compounds of the formula I are known or have been described together with processes for their production in the literature.

In formula I, $(C_{1-6})$alkyl groups preferably contain 1 to 4 carbon atoms, more preferably 1 or 2 carbon atoms, methyl groups being most preferred. $(C_{1-4})$-alkyl, -alkoxy, -alkylthio and -alkylsulfonyl groups preferably contain 1 or 2 carbon atoms. Hydroxy, alkoxy, hydroxyalkoxy, amino and alkylamino moieties of hydroxyalkyl, alkoxyalkyl, hydroxyalkoxyalkyl, aminoalkyl and alkylaminoalkyl groups $R_7$ in residues —COOR$_7$ are preferably not attached at the α-carbon atom. Suitably they are in the terminal position. Preferred alkylene moieties of hydroxyalkyl, alkoxyalkyl, hydroxyalkoxyalkyl, aminoalkyl and alkylaminoalkyl are ethylene and propylene. The alkylene moiety of cycloalkylalkyl groups is suitably methylene. Cycloalkyl moieties of cycloalkylalkyl groups are suitably cyclopropyl, cyclopentyl or cyclohexyl. By halogen is meant fluorine, chlorine or bromine, in particular chlorine.

The multiple bond in alkenyl, alkinyl and phenylalkenyl groups $R_1$ or —COOR$_7$ is preferably not in the α,β-position. Alkenyl and alkinyl groups preferably have 3 to 5 carbon atoms. Alkenyl is suitably allyl or 2-methylallyl is suitably propionyl. Phenylalkenyl groups preferably have the trans-configuration and include, e.g. cinnamyl. When $R_1$ is phenyl this is preferably unsubstituted. When $R_1$ is di- or tri-substituted phenyl, the substituents are preferably the same. Hetrocyclic rings as $R_7$, $R_8$ and $R_9$ are, e.g. furyl, thienyl, pyrrolyl, thiazolyl, isothiazolyl, thiadiazolyl, oxazolyl, isoxazolyl, oxadiazolyl, imidazolyl, pyrazolyl, triazolyl, tetrazolyl, pyridyl, pyrimidinyl, pyrazinyl, pyridazinyl, piperidinyl, morpholinyl and triazinyl. Hetercyclic rings comprised by $R_{10}$ and $R_{11}$ together with the nitrogen atom to which they are attached are preferably saturated and include pyrrolidine, piperidine, piperazine, N-alkylpiperazine and morpholine rings. $R_2$ and $R_5$ are preferably identical. $R_6$ is suitably halogen, alkyl, alkoxy, nitro or trifluoromethyl and is preferably in the o- or m-position with respect to the position of attachment of the dihydropyridine residue. When A is of formula (a), $R_6$ is preferably hydrogen.

| Compound No. | $R_1$ | $R_2$ | $R_3$ | $R_4$ | $R_5$ | $R_6$ | X | y |
|---|---|---|---|---|---|---|---|---|
| 1 | H | CH$_3$ | CN | COO—i-Bu | CH$_3$ | H | O | 4 |
| 2 | H | CH$_3$ | COOC$_2$H$_5$ | SO$_2$CH$_3$ | CH$_3$ | H | O | 4 |
| 3 | H | CH$_3$ | CN | COOC$_2$H$_5$ | CH$_3$ | H | O | 4 |
| 4 | H | CH$_3$ | CN | COOC$_2$H$_5$ | CH$_3$ | H | S | 4 |
| 5 | H | CH$_3$ | CN | COOCH$_2$CH(CH$_3$)$_2$ | CH$_3$ | H | S | 4 |
| 6 | H | CH$_3$ | COOCH$_3$ | COC$_6$H$_5$ | CH$_3$ | H | O | 4 |
| 7 | H | CH$_3$ | COO(CH$_2$)$_2$N(CH$_3$)(CH$_2$C$_6$H$_5$) | COOC$_2$H$_5$ | CH$_3$ | H | O | 4 |
| 8 | H | CH$_3$ | COO(CH$_2$)$_2$N(CH$_3$)(CH$_2$C$_6$H$_5$) | COOC$_2$H$_5$ | CH$_3$ | H | S | 4 |
| 9 | H | CH$_3$ | COO(CH$_2$)$_2$N(CH$_3$)$_2$ | COO(CH$_2$)$_2$N(CH$_3$)$_2$ | CH$_3$ | H | O | 4 |
| 10 | H | CH$_3$ | COO(CH$_2$)$_2$N(CH$_3$)$_2$ | COO(CH$_2$)$_2$N(CH$_3$)$_2$ | CH$_3$ | H | S | 4 |
| 11 | H | CH$_3$ | COO(CH$_2$)$_2$N(CH$_3$)$_2$ | COOC$_2$H$_5$ | CH$_3$ | H | O | 4 |
| 12 | H | CH$_3$ | COO(CH$_2$)$_2$N(CH$_3$)$_2$ | COOC$_2$H$_5$ | CH$_3$ | H | S | 4 |

-continued

| Compound No. | R₁ | R₂ | R₃ | R₄ | R₅ | R₆ | X | y |
|---|---|---|---|---|---|---|---|---|
| 13 | H | CH₃ | COO(CH₂)₂N(CH₃)(CH₂C₆H₅) | COOC₂H₅ | CH₃ | H | S | 5 |
| 14 | H | CH₃ | COO(CH₂)₂N(CH₃)(CH₂C₆H₅) | COOC₂H₅ | CH₃ | H | O | 5 |
| 15 | H | CH₃ | COO(CH₂)₂N(CH₃)(CH₂C₆H₅) | COOC₂H₅ | CH₃ | H | O | 4 |
| 16 | H | △ | COOC₂H₅ | COOC₂H₅ | CH₃ | H | O | 4 |
| 17 | H | △ | COOCH₃ | COOCH₃ | CH₃ | H | O | 4 |
| 18 | H | △ | COOCH₃ | COOCH₃ | △ | H | O | 4 |
| 19 | H | △ | COOC₂H₅ | COOC₂H₅ | △ | H | O | 4 |
| 20 | H | CH₃ | COO(CH₂)₂—C₆H₅ | COOCH₃ | CH₃ | H | O | 4 |
| 21 | H | CH₃ | COOCH₃ | COOCH₂C₆H₅ | CH₃ | H | O | 4 |
| 22 | H | CH₃ | COOC₂H₅ | COOC₂H₅ | CH₃ | H | O | 4 |
| 23 | H | CH₃ | COOC₂H₅ | COOC₂H₅ | CH₃ | H | S | 4 |
| 24 | H | CH₃ | COOC(CH₃)₃ | COOC(CH₃)₃ | CH₃ | H | S | 4 |
| 25 | H | CH₃ | COOCH₃ | COOCH₃ | CH₃ | 7-Cl | O | 4 |
| 26 | H | CH₃ | COOCH₃ | COOCH₃ | CH₃ | H | S | 4 |
| 27 | H | CH₃ | COOC₂H₅ | COOC₂H₅ | CH₃ | 5-OCH₃ | S | 4 |
| 28 | H | CH₃ | COOC₂H₅ | COOC₂H₅ | CH₃ | 7-Cl | S | 4 |
| 29 | H | CH₃ | COOC₂H₅ | COOC₂H₅ | CH₃ | H | S | 5 |
| 30 | H | CH₃ | COOC₂H₅ | COOC₂H₅ | CH₃ | 4-Cl | S | 5 |
| 31 | H | CH₃ | COC(CH₃)₃ | COC(CH₃)₃ | CH₃ | H | S | 4 |
| 32 | H | CH₃ | COCH₃ | COCH₃ | CH₃ | 7-Cl | O | 4 |
| 33 | H | CH₃ | COCH₃ | COCH₃ | CH₃ | H | S | 4 |
| 34 | H | CH₃ | COC₂H₅ | COC₂H₅ | CH₃ | 5-OCH₃ | S | 4 |
| 35 | H | CH₃ | COC₂H₅ | COC₂H₅ | CH₃ | 7-Cl | S | 4 |
| 36 | H | CH₃ | COC₂H₅ | COC₂H₅ | CH₃ | H | S | 5 |
| 37 | H | CH₃ | COC₂H₅ | COC₂H₅ | CH₃ | 4-Cl | S | 5 |
| 38 | H | CH₃ | COCH₃ | COCH₃ | CH₃ | H | O | 4 |
| 39 | H | CH₃ | COCH₃ | COOC₂H₅ | CH₃ | H | O | 4 |
| 40 | H | CH₃ | COCH₃ | COOC₂H₅ | CH₃ | H | S | 4 |
| 41 | H | CH₃ | COOCH₂CH(CH₃)₂ | COOCH₃ | CH₃ | H | O | 4 |
| 42 | H | CH₃ | COOCH₃ | COOCH₃ | CH₃ | H | O | 4 |
| 43 | H | CH₃ | COOC₂H₅ | COOC₂H₅ | CH₃ | H | O | 5 |
| 44 | H | CH₃ | COOCH₂CH(CH₃)₂ | COOC₂H₅ | CH₃ | H | S | 4 |
| 45 | H | CH₃ | COOCH₂CH(CH₃)₂ | COOC₂H₅ | CH₃ | H | O | 4 |
| 46 | H | CH₃ | COOC(CH₃)₃ | COOC(CH₃)₃ | CH₃ | H | O | 4 |
| 47 | H | CH₃ | COOCH₂CH(CH₃)₂ | COOCH₂CH(CH₃)₂ | CH₃ | H | O | 4 |
| 48 | H | CH₃ | COO(CH₂)₂OC₂H₅ | COOC₂H₅ | CH₃ | H | O | 4 |
| 49 | H | CH₃ | COO(CH₂)₂OC₂H₅ | COOC₂H₅ | CH₃ | H | S | 4 |
| 50 | H | CH₃ | COO(CH₂)₂OC₂H₅ | COOC₂H₅ | CH₃ | H | S | 5 |
| 51 | H | CH₃ | COOCH(CH₃)₂ | COOCH₃ | CH₃ | H | O | 4 |
| 52 | H | CH₃ | COO(CH₂)₂OCH₃ | COOCH₃ | CH₃ | H | O | 4 |
| 53 | H | CH₃ | COO(CH₂)₂OCH(CH₃)₂ | COOCH₃ | CH₃ | H | O | 4 |
| 54 | H | CH₃ | COO(CH₂)₂OC₂H₅ | COOCH₃ | CH₃ | H | O | 4 |
| 55 | H | CH₃ | COO—▽ | COOCH₃ | CH₃ | H | O | 4 |
| 56 | H | CH₃ | COO(CH₂)₂OCH₃ | COOCH(CH₃)₂ | CH₃ | H | O | 4 |
| 57 | H | CH₃ | COOCH₃ | COOC₂H₅ | CH₃ | H | O | 4 |
| 58 | CH₃ | CH₃ | COOC₂H₅ | COOC₂H₅ | CH₃ | H | O | 4 |
| 59 | n-C₃H₇ | CH₃ | COOC₂H₅ | COOC₂H₅ | CH₃ | H | O | 4 |

Suitable compounds of formula I, wherein A is a residue (b), for use in accordance with the present invention are those shown in the following table:

| Compound No. | R₁ | R₂ | R₃ | R₄ | R₅ | R₆ | x | y | m |
| --- | --- | --- | --- | --- | --- | --- | --- | --- | --- |
| 60 | H | CH₃ | COOCH₂CF₃ | COOCH₃ | CH₃ | o-Cl | — | — | 1 |
| 61 | H | CH₃ | COOCH₃ | COOC₂H₅ | CH₃ | 2,3-di-Cl | — | — | 2 |
| 62 | H | CH₃ | COOC₂H₅ | COOC₂H₅ | CH₂OH | m-NO₂ | — | — | 1 |
| 63 | H | CH₃ | COOCH(CH₃)₂ | COOCH₃ | —CN | m-NO₂ | — | — | 1 |
| 64 | H | CH₃ | COO(CH₂)₂N(CH₃)(CH₂—C₆H₅) | COOCH₃ | CH₃ | m-NO₂ | — | — | 1 |
| 65 | H | CH₃ | COOCH₃ | COOCH₃ | CH₃ | o-NO₂ | — | — | 1 |
| 66 | H | CH₃ | COO(CH₂)₂OC₃H₇ | COO(CH₂)₂OC₃H₇ | CH₃ | m-NO₂ | — | — | 1 |
| 67 | H | CH₃ | COO(CH₂)₂OCH₃ | COOCH(CH₃)₂ | CH₃ | m-NO₂ | — | — | 1 |
| 68 | H | CH₃ | COOCH₃ | COOCH₂CH(CH₃)₂ | CH₃ | o-NO₂ | — | — | 1 |
| 69 | H | CH₃ | COOC₂H₅ | COOCH₃ | CH₃ | m-NO₂ | — | — | 1 |
| 70 | H | CH₃ | COOC₂H₅ | COOC₂H₅ | CH₃ | o-CF₃ | — | — | 1 |

A suitable compound of formula I, wherein A is a residue (c), for use in accordance with the present invention is compound No. 71 wherein: $R_1$ = H, $R_2$ = CH₃, $R_3$ = COOC₂H₅, $R_4$ = COOC₂H₅, $R_5$ = CH₃, and $R_6$ = o-SCH₃.

Preferred calcium antagonists for use in accordance with the present invention are compounds 7, 21, 22, 39, 41, 45, 48, 51 to 57 inclusive, 59, 60 and 65 to 68 inclusive, in particular the compounds 21, 22, 51, 54, 55 and 65 to 67 inclusive. The most preferred calcium antagonist for use in accordance with the present invention is compound 65, 1,4-dihydro-2,6-dimethyl-4-(2-nitrophenyl)-3,5-pyridine-dicarboxylic acid dimethyl ester, also known as Nifedipin ®.

Where calcium antagonist components (b) form acid addition salts they may be used in accordance with the invention in either free or pharmaceutically acceptable acid addition salt form. Suitable pharmaceutically acceptable acid addition salts include, e.g. the hydrochlorides, hydrobromides, acetates, fumarates and maleinates.

In the preparations of the invention components (a) and (b) are suitably present in a ratio of from 1:1 to 1:50, preferably from 1:2.5 to 1:25, most preferably from 1:5 to 1:10 parts by weight (a:b).

Preparations in accordance with the invention most suitably contain components (a) and (b) in a ratio of:
(i) from about 0.5 to about 10 mg of (a): from about 0.5 to about 100 mg of (b); preferably
(ii) from about 1.0 to about 7.5 mg of (a): from about 5.0 to about 75 mg of (b); more preferably
(iii) from about 2.0 to about 5.0 mg of (a): from about 10 to about 60 mg of (b); most preferably
(iv) from about 2.0 to about 4.0 mg of (a): from about 10 to about 30 mg of (b); e.g.
(v) about 2.0 or about 4.0 mg of (a): about 20 mg of (b).

Preparations in accordance with the invention in unit dosage form, e.g. for use in the treatment of hypertension and for administration, e.g. 1× or 2× to 4× daily, suitably contain components (a) and (b) in the amounts specified under (i) to (v) above/unit dosage.

The preparations according to the invention may be prepared in conventional manner using conventional galenic techniques, e.g. by admixture of components (a) and (b) optionally together with conventional pharmaceutical excipients such as fillers, granulating agents, disintegrating agents, binding agents, lubricating agents, dispersing agents, wetting agents, dyestuffs and preserving agents.

The preparations of the invention are suitably put up in solid form, e.g. as tablets, powders, granules or capsules, or alternatively as suspensions or emulsions. Preferably they are put up in unit dosage form, particularly in unit dosage form for oral administration, e.g. as tablets, capsules or the like. Such unit dosage forms may also contain components (a) and (b) separately, e.g. in separate layers in a layer or mantel tablet or in separate compartments within a split capsule.

Component (a) is preferably present in the preparations of the invention in the form of a solid solution, e.g. obtained in accordance with the general procedures described in German Offenleungsschrift No. 29 50 145. Such solid solutions are obtained by dissolving component (a) together with an appropriate pharmaceutically acceptable polymeric material and, optionally a pharmaceutically acceptable polyoxalkylene steryl ether, in a lower alkanol, and evaporating off the lower alkanol to provide the desired solid solution.

Suitable pharmaceutically acceptable polymeric materials for the preparation of such solid solutions are in particular non-crosslinked poly-N-vinylpyrrolidone-2 polymers having an average molecular weight of from 10,000 to 100,000, especially from 11,500 to 40,000, most preferably from 20,000 to 30,000. Suitable alkanols for use in the process are in particular methanol and ethanol. Suitable polyoxyalkylene steryl ethers are in particular polyoxyalkylene cholesteryl ethers, especially polyoxyethylene cholesteryl ethers in particular the product commercially available under the trade mark SOLULAN C-24.

The solid solution comprising component (a) obtained in the above manner is suitably dried and recovered in powder form, e.g. obtained by comminution of the initially obtained polymeric material, and admixed with component (b) and optionally further pharmaceutically acceptable diluents or carriers. The thus obtained preparation may then be put up in the desired dosage form, e.g. as capsules, tablets or pellets or as a granulate. Such dosage forms are suitably provided with an enteric coating, i.e. coating resistant to dissolution by the gastric juices, again in accordance with the methods generally described in DOS 29 50 154.

Although such solid dosage forms as described above will generally be preferred, the present invention also embraces liquid preparations for example solutions for injection.

In accordance with the foregoing the present invention also provides a process for the production of a pharmaceutical preparation as hereinbefore defined, which process comprises bringing a component (a) and a component (b) into mutual association in a pharmaceutical dosable form, for example intimately admixing said components (a) and (b), suitably in the presence of a pharmaceutically acceptable diluent or carrier therefor; for example carrying out the steps comprising:

1. dissolving a component (a) and an appropriate pharmaceutically acceptable polymeric material and, optionally, a pharmaceutically acceptable polyoxyalkylene steryl ether in a lower alkanol;
2. evaporating the lower alkanol to obtain a solid solution comprising component (a) and said polymeric material, optionally together with said polyoxyalkylene steryl ether;
3. recovering said solid solution in substantially dry powder form;
4. compounding said dry powder with a component (b); and
5. formulating the admixture obtained via step 4 in solid dosage form, e.g. as a tablet, capsule, pellet or granulate; and, when required,
6. enterically coating said solid dosage form.

In yet a further aspect the present invention also provides a pack or dispenser-device adapted to facilitate the concomitant administration of a component (a) and (b) as defined above, said components (a) and (b) being contained in the pack or dispenser device apart. Conveniently the components (a) and (b) are contained in the pack or dispenser device in separated unit dosage form. Preferably the pack or dispenser device bears directions for the concomitant administration of active agents (a) and (b) at a predetermined daily dosage rate. The directions may for example be printed directly on the pack or dispenser device.

As previously indicated, in accordance with the present invention preparations comprising (a) co-dergocrine or a pharmaceutically acceptable acid addition salt thereof and (b) a calcium antagonist or pharmaceutically acceptable acid addition salt thereof possess surprisingly advantageous pharmacological/therapeutic properties, e.g. blood-pressure lowering activity, and to exhibit a particularly advantageous pharmacological/therapeutic profile, e.g. as may be evidenced by duration of activity and tolerability.

The advantageous benefits obtainable from use of components (a) and (b) in combination may be shown in standard animal tests for example in accordance with the method described by R. Hof et al. in Basic Res. Cardiol. 75, [1980] 747–756 and 76, [1981] 630–368 and in J. Cardiovasc. Pharmacol. 4 [1982] 352–362] employing "tracer" microspheres in the anaesthetised cat. in this test method coronary vasodilation, and reduction in blood-pressure may be demonstrated on i.v. administration of preparations in accordance with the present invention and comprising components (a) and (b) in a ratio of from 1:1 to 1:50 p.p.w., in particular 1:5 to 1:10 p.p.w., at dosages of from about 3 to about 300 μg/animal body weight.

The surprising effectiveness of preparations in accordance with the invention may also be shown in the wake, spontaneously hypertonic rat, according to the method described by G. M. Tschirki et. al. Arzneimittelforschung 18 [1968] 1285. In this test method preparations in accordance with the present invention and comprising components (a) and (b) in a ratio of from 1:1 to 1:50, in particular 1:5 to 1:10 p.p.w. may be shown to induce a lowering of blood pressure on administration at dosages of from about 1 to about 100 μg. In addition activity may be shown to be of surprisingly greater potency and longer duration than obtainable on administration of components (a) and (b) individually at corresponding dosage rates.

The preparations of the invention are accordingly useful for the treatment or prophylaxis of hypertension, i.e. for use as bloodpressure lowering agents.

In addition, the preparations of the invention may also be shown to possess surprisingly advantageous vasodilatory action on the capilliary vessels in the carotid region, whereby the vasoconstrictive action of serotonin is reduced and associated dysregulation inhibited. The preparations of the invention are accordingly also useful for the prophylaxis or treatment of migraine and vascular headache, for example "cluster headache", and in particular for interval treatment (prophylaxis) of migraine.

The advantageous properties of the preparations of the invention may also be demonstrated in clinical trials, e.g. involving administration of components (a) and (b) alone and in combination in trial groups of subjects exhibiting hypertension. In one such trial subjects receive individual unit dosages comprising (i) 2 mg co-dergocrine mesylate plus 20 mg Nifedipin ®, or
(ii) 4 mg co-dergocrine mesylate plus 20 mg Nifedipin ®, or
(iii) 20 mg Nifedipine ® alone; or
(iv) 2 or 4 mg co-dergocrine mesylate alone.

Each subject receives two unit dosages daily, administered each morning and evening for the duration of the trial. Dosages are administered orally and are taken with a little food and liquid. The following parameters are measured for each trial subject at regular intervals during the period immediately preceeding the trial (i.e. prior to medication) and during the course of the trial:
 -blood pressure
 -pulse
 -heart frequency
 -heart/time volume
 -peripheral resistance
 -heart-beat volume Measurements are again taken after conclusion of the trial. Results obtained prior/post-medication (control) are compared with results obtained during the trial and effectiveness of individual medication applied [(i), (ii), (iii) or (iv)] correlated.

In accordance with the foregoing the present invention also provides a method for the treatment or prophylaxis of hypertension or migraine in a subject in need of such treatment which method comprises co-administering to said subject an effective amount of (a) co-dergocrine or a pharmaceutically acceptable acid addition salt thereof and (b) a calcium antagonist or pharmaceutically acceptable acid addition salt thereof. Preferably co-administration of components (a) and (b) is effected substantially concomitantly. Most preferably components (a) and (b) are co-administered simultaneously, e.g. in the form of a preparation as hereinbefore defined.

The exact daily dosages of (a) and (b) for use in the method of the invention will of course depend on the particul-ar calcium antagonist chosen as (b) as well as upon the mode of administration, the condition to be treated and the effect desired. However in general satisfactory results are obtained on administration of unit dosages as hereinbefore described [e.g. containing from about 0.5 to about 10 mg, preferably about 1.0 to about 7.5, more preferably from about 2.0 to about 5.0, and most preferably from about 2.0 to about 4.0 mg of (a) and from about 0.5 to about 100 mg, preferably from about 5.0 to about 75 mg, more preferably from about 10 to about 60 mg, and most preferably from about 10 to about 30 mg of (b)], 1x or from 2x to 3x daily. Especially preferred daily dosages for component (a) are accordingly of the order of from 2.0 to 12.0 mg and for the preferred component (b) [Nifedipin ®] of the order of from 10 to 60 mg.

The following examples are illustrative of the processes for the production of the preparations of the invention.

Example 1

Preparation of tablets comprising 2 mg co-dergocrine mesylate and 20 mg Nifedipin ®

Composition of each product tablet

| Component | Quantity (mg) |
| --- | --- |
| (a) Co-dergocrine mesylate | 2.00 |
| (b) Polyoxyethylene-cholesteryl ether (Solulan C-24 ®) | 0.14 |
| (c) Polyvinyl pyrrolidone | 4.50 |
| (d) 1,4-Dihydro-2,6-dimethyl-4-(2-nitrophenyl)-3,5-pyridine-dicarboxylic acid dimethyl ester (Nifedipin ®) | 20.00 |
| (e) Polyoxyethylene-cholesteryl ether (Solulan C-24 ®) | 15.57 |
| (f) Cellulose | 7.93 |
| (g) Corn-starch | 2.29 |
| (h) Lactose | 109.07 |
| (i) Cellulose | 70.19 |
| (j) Amorphous SiO$_2$ (Aerosil ®) | 3.98 |
| (k) Magnesium stearate | 4.29 |
| Total | 239.96 mg |

Components (a) through c) are compounded as a solid solution. Components (d) through (g) are compounded as a granulate. The said solid solution and granulate are then tabletted together with additional components (h) through (k). The individual steps are performed as follows:

(A) Preparation of solid solution 15.0 g of (a), 1.5 g of (b) and 33.95 g of (c) (average mol. wt.=25,000) are added to 250 ml methanol in a 1 liter flask, and the flask connected to a rotary evaporator. The contents of the flask are heated to 60° C. with rotation of the flask, on a water bath at 60° C., to give a clear solution. The methanol is evaporated under reduced pressure at 60° C. until the flask contents reach a syrupy consistency. The obtained mass is placed in an evaporating dish and allowed to stand for 2 hours at room temperature and is then dried in a vacuum drying cupboard at 30° C. and ca. 1 Torr. for 12 hours, ground to a powder and further dried.

(B) Preparation of granulate 43.48 g of (d) and 34.13 9 of (e) are dissolved in methanol. 17.39 g of (f) and 5.0 g of (g) are suspended in the obtained solution and the whole is evaporated to dryness.

(C) Preparation of tablets:

19.17 g of the granulate obtained according to (B), 2.79 g of the powdered solid solution obtained according to (A), 45.81 g of (h), 29.48 g of (i), 1.67 g of (j) and 1.8 g of (k) are thoroughly mixed and pressed into 239.96 mg tablets having the composition given above. The obtained tablets may be optionally enterically coated with a solution comprising

| Component | Quantity (g) |
| --- | --- |
| (l) cellulose acetate-phthalate (CAP) | 90.00 |
| (m) di-n-butylphthalate | 22.50 |
| (n) acetone | 240.00 |
| (o) ethanol | 21.00 |
| (p) dichloromethane | 526.50 |
| Total | 900.00 g |

The coating is applied using a hand spray pistol at a spray-pressure of from 1.0 to 1.5 bar using known interval-spraying technique until each tablet core has a 10 mg coating comprising (l) plus (m).

EXAMPLE 2

Preparation of tablets comprising 4 mg co-dergocrine mesylate and 20 mg Nifedipin ®

Example 1 is repeated but employing the following quantities at step (c):

19.17 g of granulate obtained according to step B, 5.58 g of powder obtained according to step A, 44.16 g of (h), 28.34 g of (i), 1.67 9 of (j) and 1.8 g of (k). The obtained tablets each comprise ingredients (a) through (k) as set forth in example 1 in the following quantities (m(g).

(a) —4.00; (b) —0.28; (c) —9.00; (d) —20.00; (e) —15.57; (f) —7.93; (g) —2.29; (h) —105.14; (i) —67.48; (j) —3.98; (k) —4.29 TOTAL: 239.96 mg.

The tablets may, if desired be enterically coated as described in example 1.

We claim:

1. A method of treating hypertension comprising co-administering to a subject in need of such treatment:
    (a) co-dergocrine or a pharamceutically acceptable acid addition salt thereof; and
    (b) as a calcium antagonist, a compound selected from the group consisting of
        4-(2,1,3-benzoxadiazol-4-yl)-1,4-dihydro-2,6-dimethyl-3-ethoxycarbonyl-5-pyridine carboxylic acid ethyl ester,
        4-(2,1,3-benzthiadiazole-4-yl)-1,4-dihydro-2,6- -dimethyl-3-methoxycarbonyl-5-pyridine carboxylic acid methyl ester and 4-(2,1,3-benzoxadiazol-4-yl)-1,4-dihydro-2,6-dimethyl-3-isopropoxycarbonyl-5-pyridine carboxylic acid methyl ester;
said components (a) and (b) being co-administered in a ratio of 1:1 to 1:50 p.p.w.

2. A method of treating migraine headaches comprising co-administering to a subject in need of such treatment:
    (a) co-dergocrine or a pharmaceutically acceptable acid addition salt thereof; and
    (b) as a calcium antagonist, a compound selected from the group consisting of 4-(2,1,3-benzoxadiazol-4-yl)-1,4-dihydro-2,6-dimethyl-3-ethoxycarbonyl-5-pyridine carboxylic acid ethyl ester, 4-(2,1,3-benzthiadiazole-4-yl)-1,4-dihydro-2,6-dimethyl-3-methoxycarbonyl-5-pyridine carboxylic acid methyl ester and 4-(2,1,3-benzoxadiazol-4-yl)-1,4-dihydro-2,6-dimethyl-3-isopropoxycarbonyl-5-pyridine carboxylic acid methyl ester;
said components (a) and (b) being co-administered in a ratio of 1:1 to 1:50 p.p.w.

3. A method according to claim 2 wherein co-administration of (a) and (b) is effected substantially concomitantly.

4. A method according to claim 1 wherein co-administration of (a) and (b) is effected substantially concomitantly.

5. A pharmaceutical preparation useful in treating hypertension and migraine headaches comprising:
   (a) co-dergocrine or a pharmaceutically acceptable acid addition salt thereof; and
   (b) as a calcium antagonist, a compound selected from the group consisting of
       4-(2,1,3-benzoxadiazol-4-yl)-1,4-dihydro-2,6-dimethyl-ethoxycarbonyl-5-pyridin carboxylic acid ethyl ester,
       4-(2,1,3-benzthiadiazole-4-yl)-1,4-dihydro-2,6-dimethyl-3-methoxycarbonyl-5-pyridine carboxylic acid methyl ester and 4-(2,1,3-benzoxadiazol-4-yl)-1,4-dihydro-2,6-dimethyl-3-isopropoxycarbonyl-5-pyridine carboxylic acid methyl ester;

said components (a) and (b) being present in the pharmaceutical preparation in a ratio of 1:1 to 1:50 p.p.w.

6. A preparation according to claim 5, wherein (a) is co-dergocrine mesylate.

7. A preparation according to claim 5 wherein the ratio is 1:2.5 to 1:25 p.p.w.

8. A preparation according to claim 7 wherein the ratio is 1:5 to 1:10 p.p.w.

9. A preparation according to claim 5 wherein (a) and (b) are present in a ratio of 0.5 to 10 mg: 0.5 to 100 mg (a:(b).

10. A preparation according to claim 9 wherein the ratio is 1.0 to 7.5 mg: 5.0 to 75 mg.

11. A preparation according to claim 10 wherein the ratio is 2.0 to 5.0 mg: 10 to 60 mg.

12. A preparation according to claim 11 wherein the ratio is 2.0 to 4.0 mg: 10 to 30 mg.

13. A preparation according to claim 12 wherein the ratio is 2.0 or 4.0 mg: 20 mg.

14. A preparation according to claim 5 in unit dosage form.

15. A preparation according to claim 14 and comprising (a) and (b) in an amount of from 0.5 to 10 mg of (a) and 0.5 to 100 mg of (b).

16. A preparation according to claim 8 wherein the ratio is 1:10 p.p.w.

17. A preparation according to claim 13 wherein the ratio is 2.0:20 mg.

18. A preparation according to claim 14 comprising (a) and (b) in an amount from 1.0 to 7.5 mg of (a) and 5.0 to 75 mg of (b).

19. A preparation according to claim 5 in solid, enteric-coated form wherein component (a) is in the form of a solid solution of a pharmaceutically acceptable non-cross-linked poly-N-vinyl-pyrrolidone-2-polymer having an average molecular weight of from 10,000 to 100,000 and a pharmaceutically acceptable polyoxyalkylene cholesteryl ether.

* * * * *